United States Patent
Semerdjian et al.

(10) Patent No.: US 6,174,352 B1
(45) Date of Patent: Jan. 16, 2001

(54) ROUND PROFILE MULTI-CAPILLARY ASSEMBLY AND METHOD OF MAKING

(75) Inventors: Roy V. Semerdjian, Sacramento; David A. Le Febre, Camino, both of CA (US)

(73) Assignee: UOP LLC, Des Plaines, IL (US)

(*) Notice: Under 35 U.S.C. 154(b), the term of this patent shall be extended for 0 days.

(21) Appl. No.: 09/198,471

(22) Filed: Nov. 24, 1998

(51) Int. Cl.⁷ .............................. B01D 15/08; B01D 71/04
(52) U.S. Cl. .................................. 96/8; 96/101; 55/522; 55/DIG. 5
(58) Field of Search ................................ 95/83; 96/8, 10, 96/101–107; 55/522, 527, DIG. 5

(56) References Cited

U.S. PATENT DOCUMENTS

| | | | |
|---|---|---|---|
| 3,100,868 | * 8/1963 | McAfee, Jr. | 96/8 X |
| 3,262,251 | * 7/1966 | Hicks, Jr. | 96/8 |
| 3,269,817 | * 8/1966 | Bondley | 96/8 X |
| 3,279,902 | * 10/1966 | Gardner | 96/8 X |
| 3,294,504 | * 12/1966 | Hicks, Jr. | 96/8 X |
| 4,293,415 | 10/1981 | Bente, III et al. | 210/198.2 |
| 4,424,127 | * 1/1984 | Roeraade | 96/104 X |
| 4,657,742 | * 4/1987 | Beaver | 96/8 X |
| 4,689,255 | * 8/1987 | Smoot et al. | 96/8 X |
| 4,872,979 | * 10/1989 | Golay | 96/107 X |
| 5,092,155 | * 3/1992 | Rounbehler et al. | 96/104 X |
| 5,234,594 | 8/1993 | Tonucci et al. | 210/500.26 |
| 5,498,324 | 3/1996 | Yeung et al. | 204/452 |
| 5,551,278 | * 9/1996 | Rounbehler et al. | 96/101 X |
| 5,552,042 | 9/1996 | Le Febre et al. | 210/198.2 |
| 5,584,982 | 12/1996 | Dovichi et al. | 204/603 |
| 5,653,777 | 8/1997 | Semerdjian | 65/17.2 |
| 5,692,078 | * 11/1997 | Le Febre | 385/53 |

FOREIGN PATENT DOCUMENTS

| | | |
|---|---|---|
| 61-265567 | 11/1986 | (JP) . |
| 62-150162 | 7/1987 | (JP) . |
| 63-002824 | 1/1988 | (JP) . |
| 09 043223 | 2/1997 | (JP) . |

OTHER PUBLICATIONS

"How Many Wires Can Be Packed Into a Circular Conduit?" by Jacques Dutka, *Machinery*, Oct. 1956, pp. 245–246 and pp. 74–79.

* cited by examiner

Primary Examiner—Robert H. Spitzer
(74) Attorney, Agent, or Firm—John G. Tolomei; James C. Paschall (57) ABSTRACT

A multi-passage capillary arrangement can be formed from ductile glass material into an assembly that has an essentially round outer cross section and multiple capillary passages with diameters of 250 micrometers or less. The multiple capillary assembly provides multiple capillary sized passages of a regularly recurring shape in a single cohesive bundle. The round outer cross section facilitates the use of the multiple capillary by providing a suitable surface for connections. The multiple capillary arrangement can be made by a method that provides uniform or nearly uniform capillary passages throughout the arrangement. The capillaries are useful for chromatograph applications and as flow restrictors.

27 Claims, 4 Drawing Sheets

ROUND PROFILE MULTI-CAPILLARY ASSEMBLY AND METHOD OF MAKING

FIELD OF THE INVENTION

This invention relates to a capillary assembly especially useful in gas liquid and gas solid partition chromatography. In particular, the invention relates to a single conduit that contains multiple capillary sized passages.

BACKGROUND OF THE INVENTION

Although glass capillary and open tubular columns had been used in gas chromatography for some time, their usefulness was limited by their fragility and chemical reactivity. Because of surface hydroxyls, characteristically present on glass surfaces, the peak shapes of reactive materials such as phenols, amines, and mercaptans inter alia tended to be distorted even when the glass surface was deactivated. Thus, in the "early" gas chromatographic days of capillary and open tubular columns the many advantages of glass capillary and open tubular columns were accompanied by serious disadvantages.

In about 1980 the situation changed remarkably based on art taught by U.S. Pat. No. 4,293,415. The '415 patent taught that silica capillary columns for gas chromatography could be made in much the same manner as hollow optical fibers, e.g., liquid core quartz fibers. After treatment of the silica surface with deactivating agents the same as, or analogous to, those used for glass columns, more symmetrical peaks were obtained in gas chromatography and the patentee's silica columns even could be used for classes of compounds for which glass columns were unsatisfactory, as for example phenols, volatile carboxylic acids, mercaptans, and aliphatic amines.

U.S. Pat. No. 5,552,042 discloses a silica capillary or open tubular assembly wound on and fused to a mandrel, with the entire assembly being annealed so as to present a relatively stress free, rigid winding. The relative lack of stress eliminated the need for any external coating. The rigidity of the assembly allowed the deposit of brittle coatings, especially of inorganic materials, within the capillary or tubes as a stationary phase and usefully employed over extended time periods.

In the present state of the art a capillary column can have a larger sample capacity by increasing its bore and applying a thicker stationary phase or it can have higher plate efficiency by reducing its bore diameter and using a thinner stationary phase. A way of getting both benefits simultaneously is to use a multi-capillary. A multi-capillary is a grouping of many capillaries all bundled together. This results in a Van Deemter curve that is relatively flat compared to conventional single capillary columns. The benefits of a multi-capillary have been known for several decades but such has not been commercially implemented because of the difficulties in manufacturing a multi-capillary using conventional glass capillary drawing techniques.

Image intensifiers, also known as night vision scopes, use a structure comprising bundles of fibers. The method for manufacturing the fiber bundle for a night vision scope draws a circular glass tube through a hex die. The resultant hex shaped tubes with circular holes are then grouped together and drawn together as an assembly to form a fused bundle of reduced cross-section. The external hex shape of individual capillaries facilitates the packing together of a grouping of capillaries., i.e. similar to a bee's honeycomb.

It is known in the art to make a multi-passage capillary assembly by using hollow tubes instead of fibers. The circular holes in such a bundle are ordered with no void space in the walls and the assembly can become very large. A variation of this method casts each starting hexagonal member instead of die drawing.

One problem with the current art is that the glass used in image intensifiers is typically a low melting point lead glass. Lead glass can be easily cast or shaped through a die to form the required external hex pattern. However, the low melting point of the lead glass results in a structure that is stiff and easy to shatter. Generally, the higher the melting point of a glass the greater the elasticity. Lead is a very low melting point glass and hence has a low modulus of elasticity and a further problem of chemical erosion. But the biggest disadvantage to this approach is the resultant final shape of the assembly which is a hex. Since the ends of the multi-capillary need to be attached to other parts in a gas chromatograph, the hex shape causes difficulties in getting compression type fittings to interface.

The problem of making connections to capillary structures is not a trivial one. The fine diameters of tubing and the low tensile strength of capillary column materials, such as fused silica, makes the arrangement of capillary columns and of capillary connectors for the capillary tubes especially difficult. The problems are particularly troublesome when connecting the termini of a capillary or, in case of rigid capillary assemblies, the termini of open tubular helical coils to GC instrument conduits. Although many methods and procedures for making such connections are possible the connections generally require bonding to a conduit that has a circular cross-section. Suitable connection arrangements are described in U.S. Pat. No. 5,692,078.

The obvious solution is to make the outer cross section of the multi-capillary a circle for a more compatible fit to conventional compression fittings. This approach though confronts a mathematical problem that nobody has solved and that is: small circles in a larger circle do not pack in a uniform manner. This problem has presented itself in many different forms over the last several hundred years in stranded steel cables, in electrical conduits, etc. Simply put, circles packed together do not want to form an outer shape of a circle—circles packed together with the proper number of elements form hex shaped outlines.

It is an object of this invention to provide a multi-passage capillary assembly that has high ductility and a cross section compatible with the necessary fittings for supplying fluid to the capillary.

It is further object of this invention to provide a multi-passage capillary assembly that provides a high degree of uniformity in the individual cross sections of the multiple capillaries and has an outer cross section of the assembly that is compatible with the necessary fittings for supplying fluid to the capillary.

SUMMARY OF THE INVENTION

This invention accomplishes these objectives with a multi-passage capillary arrangement that can be formed from ductile glass material into an assembly that has an essentially round outer cross section and multiple capillary passages of a size of 250 micrometers or less. The multiple capillary assembly is characterized by multiple capillary sized passages of a regularly recurring shape, referred to as regular capillaries, that are formed together into a cohesive bundle by an outer wall having an essentially circular wall. Cohesion of the bundle refers to at least a portion of the regular capillaries sharing common internal walls that define the capillaries.

The assembly is typically in the form of a tube that defines the outer circular wall and that retains the internal capillary flow area. In most applications it is preferred that the regularly recurring shape of the capillary cross section also define capillaries of the same size. The regularly recurring shape of the capillary cross sections is typically round but may take on oval and rectilinear shapes as well.

The multi-capillary arrangement of this invention is formed by drawing down an assembly of smaller conduits surrounded by a larger outer tube until the diameter of the inner conduits have been reduced to the desired capillary size. It has been specifically found that minimizing the inner diameter of the outer containment tube for the number of capillary forming conduits contained therein dramatically increases the volume of regular capillaries formed during the drawing process.

Accordingly in a broad embodiment this invention is a multi-capillary tube comprising an outer wall having a substantially circular perimeter that surrounds an axially extending open area. Internal walls within the outer wall define a plurality of regular capillary passages. The diameter of the outer wall usually varies from 0.3 to 3.0 mm. Preferably at least 50% of the internal wall volume between adjacent capillaries is integrally bonded. The regular capillary passages extend through the tube to define at least a portion of the open area and have transverse cross sections of substantially the same shape. The maximum dimension of the regular capillaries does not exceed 250 micrometers and preferably does not exceed 60 micrometers. The minimum dimension of the capillaries to function in any application is usually 2 micrometers. Collectively, the open area defined by regular capillaries accounts for at least 20% of the total transverse cross-sectional area surrounded by the outer wall. The regular capillary passages have a substantially round cross-section and together typically account for not less than 90% of the total open area. The variation in diameter taken along any two lines of direction within the substantially circular perimeter of the tube will preferably be less than 15%. Dimensions defining the regular capillary passages will preferably vary by no more than 15%. The outer wall of the multi-capillary tube may be formed thicker than the internal walls separating the capillaries. The average thickness of the outer wall may exceed the average internal wall thickness by at least 50% and more often by a factor of 2. The outer wall may also be made of a different material than the inner walls.

In a more specific embodiment this invention is a multi-capillary tube comprising an outer wall having a substantially circular perimeter that surrounds an axially extending open area. Internal walls within the outer wall define a plurality of round capillary passages. The round capillary passages extend through the tube to define at least a portion of the axially extended open area. The round capillary passages having a substantially circular cross section and maximum diameters of 250 micrometers or less to collectively define a regular capillary open area that accounts for at least 20% of the total cross-sectional area surrounded by the outer wall. The variation in diameter taken along any two lines of direction within the substantially circular cross section of each capillary passage is not more than 15%. This small difference in the out of roundness of the capillaries will have an insignificant effect on the performance of the assembly in most applications and in particular in applications involving chromatography.

An important feature of this invention is the provision of the essentially round outer cross section with minimal internal passages that deviate from the regularly recurring shape. The internal open area defined by regular capillaries, those with cross sections in the form of the same regularly recurring shape, will equal at least 80% and more preferably at least 90% of the total internal open area through the assembly. Any remaining flow area through the assembly is typically in the form of irregular capillary passages having individual cross sectional areas that are less than the individual cross sectional areas of the regular capillary passages. Typically the irregular capillaries will have an average cross sectional area that equals 50% or less of the average flow area of the regular capillaries. Furthermore, each individual irregular capillary in a single assembly will often have a flow area that equals 50% or less than the average flow area of the regular capillaries. The relatively small diameter of the irregular capillaries minimizes the detrimental effect that the presence of the irregular capillaries may have on the different applications for the structure of the assembly of this invention. This is particularly true in the case of fluid flow applications through the capillaries where the small and usually relatively narrow configuration of the irregular capillary passages geometrically increases flow resistance relative to the regular capillaries.

Even further minimization of the effects of irregular capillaries is achieved by the deposition of materials on the surface of the capillary passages. For example, in chromatography a coating comprising an organic stationary phase or an inorganic stationary phase will normally cover at least a portion of the interior walls of the capillaries. Deposition of such materials will disproportionately reduce the effective flow diameter of the irregular capillaries relative to the regular capillaries.

The preferred structure of this invention is a uniform multi-capillary assembly that virtually eliminates the presence of irregular capillaries. In this preferred structure the internal open area defined by regular capillaries will equal at least 95% and more preferably at least 99% of the total internal open area through the assembly. The most preferred form of this structure eliminates all irregular capillaries. Furthermore, any irregular capillaries that are found in the preferred structure will have minimal effect. Any such irregular capillary will have an open area equal to 10% or less than the open area of any regular capillary. In these arrangements virtually complete elimination of the irregular channels can be accomplished by increasing the minimum internal wall thickness between the regular capillaries toward the periphery of the multi-capillary tube.

The capillary assembly of this invention has a variety of applications. A basic application is in conducting fluids for chromatography as previously described. The assembly will also find diverse uses outside the field of chromatography. Its use as a flow restrictor for regulating the discharge of hazardous fluids presents a simple application for the assembly outside the field of chromatography. The multi-capillary may also provide a beneficial structure for capillary electrophoresis that increases the practicality of collecting relatively large samples. In more diverse applications all or a portion of the capillary passages may serve as mini-conduits for retaining metallic wires or other materials with a dissimilar composition from the material defining the capillary passages or the outer wall of the assembly.

The outer wall and the inner walls of the mutlicapillary assembly may be made from any material that is suitably formed into the required structure. Thus the resulting capillary structure has an operating temperature that is limited by the stability or transition temperature of the material and any stationary phase coated on the inside of the capillaries. Drawing techniques used for forming glass fibers and tubes lend themselves most readily to the production of the tube structure of this invention. Suitable glass materials include lead silicate, borosilicate, conventional glasses (soda lime silicate), and other forms of high purity silica such as quartz or fused silica. A particularly preferred glass material is an alumino-silicate.

Once formed, an outer sleeve may surround the tube to provide additional support and structural integrity. Metallic materials will work well as outer sleeves. An especially beneficial arrangement may shrink a metallic sleeve around a glass multi-capillary assembly to compress the tube into the sleeve. An arrangement of this may provide the needed structural support for imposing the necessary ultra-high pressures that are required to push many fluids through capillaries that approach 2 micrometers in diameter.

Another aspect of this invention is a forming method that readily provides the assembly of the structure of this invention and in particular the uniform multi-capillary assembly of this invention. The method forms the multi-capillary tube or conduit with a substantially circular perimeter that surrounds a plurality of regular capillary passages defined by internal walls within an outer wall. The method starts with inserting a plurality of smaller conduits into a surrounding tube to form a tube and conduit assembly. The conduits may be formed by drawing down the tube stock to the desired conduit size. The number of inserted conduits will correspond closely with the number of regular capillaries obtained by the forming method. Common openings of the conduits are sealed about one end of the tube and conduit assembly to form a drawing stock having a closed end about which all conduits are sealed from fluid flow and an opposite open end about which all conduits are open for fluid flow. The drawing stock is then heated to a softening temperature in a suitable drawing apparatus. Simultaneously drawing the heated drawing stock while restricting fluid flow from the open conduit ends of the drawing stock reduces the interiors of the conduits to capillary size while preventing collapsing closure of the conduit interiors. A multi-capillary tube that has a number of capillary passages substantially equal to the number of conduits may be recovered from the stretched and cooled drawing stock. In many cases the reduction of the diameter of the conduits during the drawing of the heated drawing stock provides sufficient reduction in the diameter at their open ends to suitably restrict gas flow out of the interiors of the conduits to a rate that maintains the desired final diameter of the capillary passages formed from the conduits.

Preferably the conduits will again have a round cross section. Prior to drawing, the conduits in the tube and conduit assembly will preferably have a diameter in a range of from 0.5 to 1 mm and a wall thickness of from 100 to 300 micrometers. The multi-capillary assembly will usually contain at least 7 regular capillary passages. The thickness of the outer tube will usually average from 1 to 4 mm. The inner diameter of the outer tube will be determined by the number and outer diameter of the inner conduits. The most effective packing arrangement for the inner conduit has been found to be a number of circular rings of conduits that surround a central conduit. Jacques Dutka, in Machinery Journal, October 1956, gives the maximum number of small circles that may be packed into a larger circle for a number of different packing arrangements. Based on these formulas it has been found that for this invention the typical number of total passageways in a given number of passageway rings is best given by the formula for maximizing circles as presented in the foregoing reference. Therefore, where the desired arrangement for round conduits is as an assembly of rings about a central tube, the number of conduits in the assembly is determined by:

$$N=3n^2+3n+1;$$

where,
N=the total number conduits, and
n=the number of rings of conduits around the central conduit.

Where all of the inner conduits have the same outer diameter the preferred inner diameter of the outer tube is calculated in terms of a "K" factor defined by the above reference. Accordingly the outer tube has an inner diameter "D" determined by the outer diameter "d" of the inner conduits where:

$$D=K*d$$

The factor K varies mathematically with the number of inner conduits. Values for K are set forth in the above reference. Examples of specific "K" values are set forth in Table 1 for arrangements that wrap rings of conduits around a central conduit.

TABLE 1

| # of inner conduits | I.D. of Outer tube | # of inner conduits | I.D. of Outer tube |
|---|---|---|---|
| 2–7 | 3 | 122–127 | 13 |
| 8–13 | 4.465 | 128–139 | 13.166 |
| 13–19 | 5 | 140–151 | 13.490 |
| 20–31 | 6.292 | 152–163 | 14.115 |
| 32–37 | 7.001 | 164–169 | 14.857 |
| 38–43 | 7.929 | 170–187 | 15 |
| 44–55 | 8.212 | 188–199 | 15.423 |
| 56–61 | 9.001 | 200–211 | 16.100 |
| 62–73 | 9.718 | 212–223 | 16.621 |
| 74–85 | 10.166 | 224–235 | 16.875 |
| 86–91 | 11 | 236–241 | 17 |
| 92–97 | 11.393 | 242–253 | 17.371 |
| 98–109 | 11.584 | 254–262 | 18.089 |
| 110–121 | 12.136 | | |

In order to reduce the occurrence of irregular capillaries, conduits with a thicker wall section are packed toward the outside of the assembly. Wall thickness of the conduits may be increased incrementally with increasing distance from the center of the tube. However, in some assembly draws, particularly as the number of packed conduits increases, minimum irregular channels were produced by uniformly increasing the wall thickness of all of the conduits in one or two of the outermost rows. The wall thickness selection of the conduits to minimize irregular channel formation will vary with size and number of the desired capillaries as well as the material of the assembly. The additional conduit wall thickness is preferably maintained by decreasing the inside diameter of the conduits. Surprisingly, it has been observed that the conduits with increased wall thickness tend to produce slightly larger capillaries than the capillaries produced by conduits with relatively thinner walls.

Another important parameter when seeking to minimize irregular channel formation is temperature uniformity during the drawing process. It has been found that the drawing apparatus should not permit substantial temperature variations during the drawing operation. Temperature variations should be held to less than 5° C. over the length of the draw.

DESCRIPTION OF THE PREFERRED EMBODIMENTS

Figure 1:
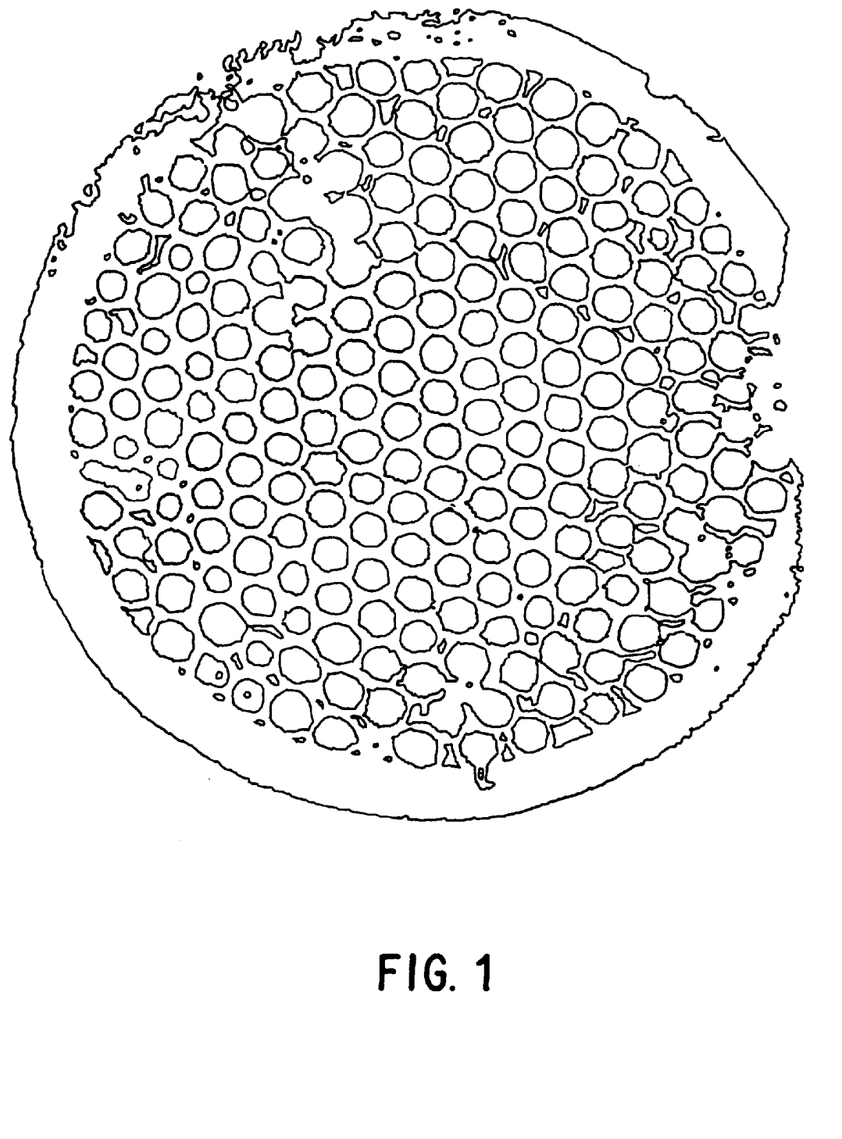
FIG. 1 is a cross-sectional view taken across a multi-capillary assembly that is not suitable for this invention.

FIG. 1 shows a drawn bundle of a random packing of capillary tubes in a larger outer tube. Although there is some order, the diameter of individual capillaries vary and there are several voids spaces with varying cross sectional areas. This pattern is unsatisfactory as a multi-capillary because too many capillaries have widely disparate dimension and diameters. In additions there are broken walls between many of the capillaries leading to large effective diameters for some of the passages. The carrier gas velocity through the capillaries is dependent on the effective diameters of the individual capillaries. When the diameters of the capillaries vary too much, peak spreading of the chromatography output unacceptably distorts results. More uniform diameters of the capillaries would produce better chromatography.

To improve on the uniformity of the individual capillary diameters and still retain an outer circular diameter the packing approach used the previously defined equation, $N=3n^2+3n+1$, to fill the circular inside of the large tube with smaller individual circles that initially define the capillary forming conduits and to set the inner diameter of the outer tube with the relationship $D=K*d$. The first several layers formed by the rings of conduits approximate a hex pack configuration but as the layers of rings get larger (n>6) the layers appear to form a circle with some void space. Drawing of the packed assembly produces a second cross section that is more regular than the randomly packed cross section of FIG. 1.

Figure 2:
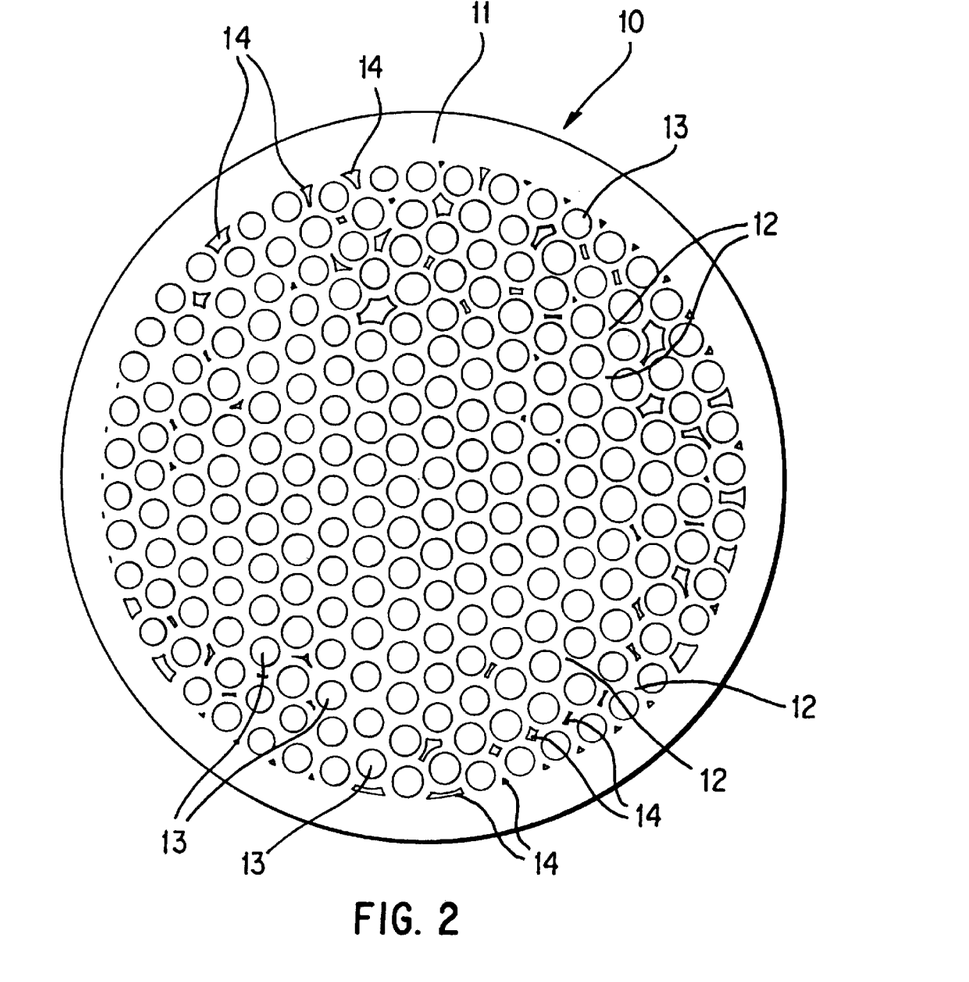
FIG. 2 is a cross-sectional view taken across a multi-capillary assembly of this invention.

FIG. 2 is a representation of a cross-section that shows the result of drawing a bundle of conduits in a larger outer tube where the conduits are packed in an ordered manner of this invention using the number of conduits predicted by the foregoing equation. The drawing process produces the multi-capillary structure 10 that has an outer wall 11 encircling a plurality of internal walls 12. Internal walls 12 define regular capillaries 13 and irregular capillaries 14. The upper left hand region of the tube shows fracture damage that occurred when cutting the tube and not tube forming imperfections. Although not perfect, there is order to the regular capillaries. In addition the individual diameters of the regular capillaries are fairly uniform. While the dimension of the irregular capillaries vary widely, their total area comprises a relatively small amount, less than 1% of the total open area of structure 10. Basically the irregular capillaries constitute regions where the walls of the conduits that initially define the capillaries during the drawing process did not completely bond. Nevertheless, the structure of FIG. 2 shows a high percentage of integral bonding between the walls separating the capillaries.

The pattern of FIG. 2—although containing defects—can be used advantageously in some applications. The presence of the irregular capillaries can result in some distortion of results when used in chromatography applications. Since the carrier gas velocity is dependent on the individual capillary diameter, each irregular capillary will have a different carrier velocity relative to all of the regular capillaries and the other irregular capillaries. If the diameters and the resulting velocities of the capillaries vary too much, unacceptable peak spreading will result. While completely uniform diameters produce the best chromatography, a sufficient minimization of the irregular capillaries will provide acceptable results for many applications.

A number of different forming techniques and material properties are important to obtaining the uniform multi-capillary structure. Drawing the structure from conduits themselves having very uniform bores and walls enhances the uniformity of the resulting structure. Uniformity of the individual conduits may be enhanced by drawing the starting conduits down in several stages from large conduits. Uniformity of the resulting capillaries also improves as the alignment of the conduits in the drawing stock becomes more parallel.

Figure 3:
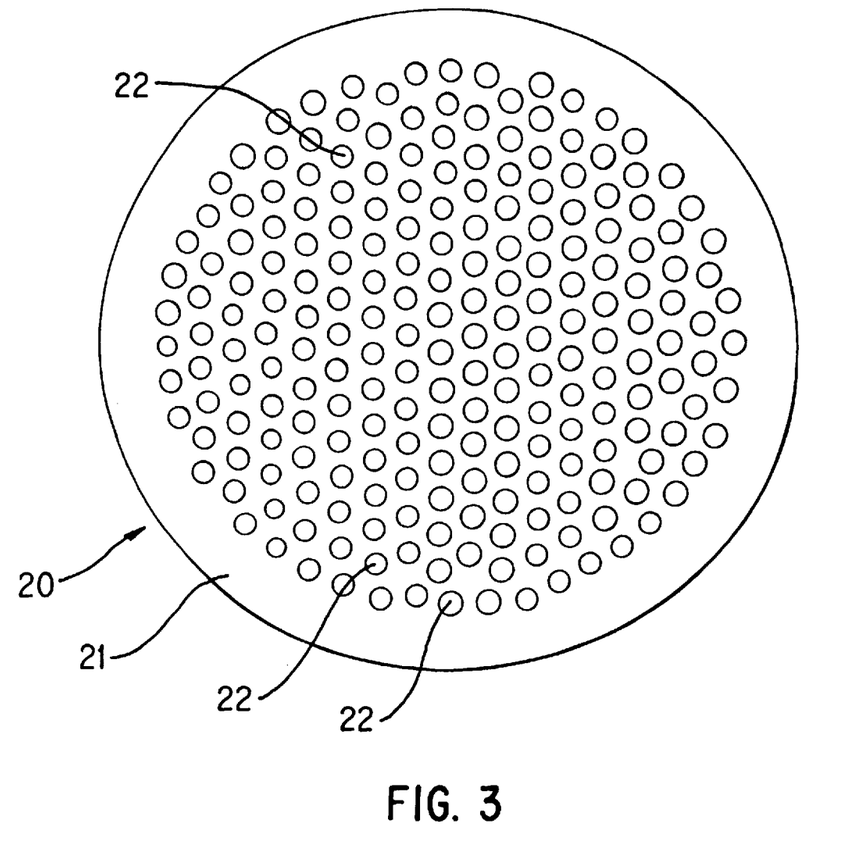
FIG. 3 is a cross-sectional view taken across another multi-capillary assembly of this invention.

FIG. 3 shows a representation of a cross-section of a multi-capillary structure 20 that eliminates the irregular channels. The structure of FIG. 3 provides a near perfect solution to the problem of providing uniform capillaries 21 in a tube 22 having a circular outside. FIG. 3 does show some variances in diameters between different capillaries and some minor ovaling of some capillaries. The minor irregularities will not have a significant impact on the application of the multi-capillary for chromatographic applications. The ovality of the passages will have minimum changes on the flow characteristics through such capillary passages. The small percentage of capillary passages with reductions in diameter will similarly have little negative affect on the chromatography results due to their small number and the regular overall shape of the capillary passages.

Forming the capillary structure of FIG. 3 relies on increasing the wall thickness of the last two or three rows to provide enough material to fill in the void space of the outer rows that can be seen in FIG. 2. The additional wall thickness of the outer walls reduces the void area of the total cross-sectional area surrounded by the outer wall to near zero such that the regular capillary flow area accounts for at least 95% of the total flow area through the multi-capillary. The surface tension of the outer containing tube and all of the enclosed conduits, when heated to their softening point, is sufficient to collapse the total assembly to a near void free cross section. Almost all of the conduits that start with thicker walls have the same inner diameter as the other inner tubes in the assembly. For a 217 capillary assembly the outer rows 7 and 8 have increased wall thickness of 4 and 8 percent, respectively. This results in the cross section of FIG. 3 showing a smaller fraction of voids. The structure has 217 capillaries with diameters of about 40 $\mu$M all within a tube with an outer diameter of about 1.2 mm. The wall thickness chosen for the outer rows can be varied depending on the draw ratio and the temperature of the draw.

As an example of a forming technique for the capillary tubes of this invention, the multi-capillary shown in FIG. 3 was formed by the following method. The outer tube and 217 inner conduits had the following properties:

| | |
|---|---|
| outer tube I.D./O.D. | 12.7/15.2 mm |
| inner tube I.D./O.D. | 0.564/0.764 mm |
| glass material | aluminosilicate glass |
| glass melting point | 1120° C. |

To increase the uniformity, the wall thickness of the outer two rows of tubes was increased as described above. Whether used with uniform conduits or conduits with the varied thickness or diameters the starting conduits have their top ends capped to inhibit gas flow in the tubing. This prevents the tubes from collapsing and forming a solid rod during the drawing process. The structure for the drawing stock is assembled one row of conduits at a time using glue or rubber bands to hold each row in place. The thicker outer walled tubing is added in the same manner. The assembly is mounted in the drawing tower and allowed to slowly equilibrate at the softening temperature of the glass. This begins to establish the surface forces on the initial part of the assembly and corrects for slight packing errors. The tip of the preform is then dropped and a tractor is used to draw the preform structure from the furnace.

The drawing furnace was operated in the following manner:

| | |
|---|---|
| top feed rate | 1 mm/min |
| bottom feed rate | 190 mm/min |
| carrier gas flow (He) | 6 L/min |
| furnace temperature | 983° C. |

Capillaries of other sizes may be produced in varying numbers using the same formula and approach of increasing the wall thickness of the last two or three rows in a progressive manner. Even if the number of rows is less than six, the outer rows must be increased in wall thickness to avoid a hex shaped outline and/or voids. The greater the number of rows, the more outer rows that need to have thicker walls.

A similar reduction in irregular capillaries can be achieved by using solid rods on the outer periphery of the bundle to produce a symmetric pattern. However, this technique seems to produce more anomalous behavior than the increased wall thickness of the outer rows and frequently distorts the inner and outer pattern of holes.

While not confirming any particular theory about the manner in which the method forms the tubes it is believed that during the drawing process of the assembly, surface tension of the outer structure forces the assembly to conform to its least geometric energy state, relying on a symmetrical distribution of surface tensions of both the outer surface of the assembly and the inner surfaces of the bores coupled with bore pressurization to form a uniform pattern of holes with no void space.

Figure 4:
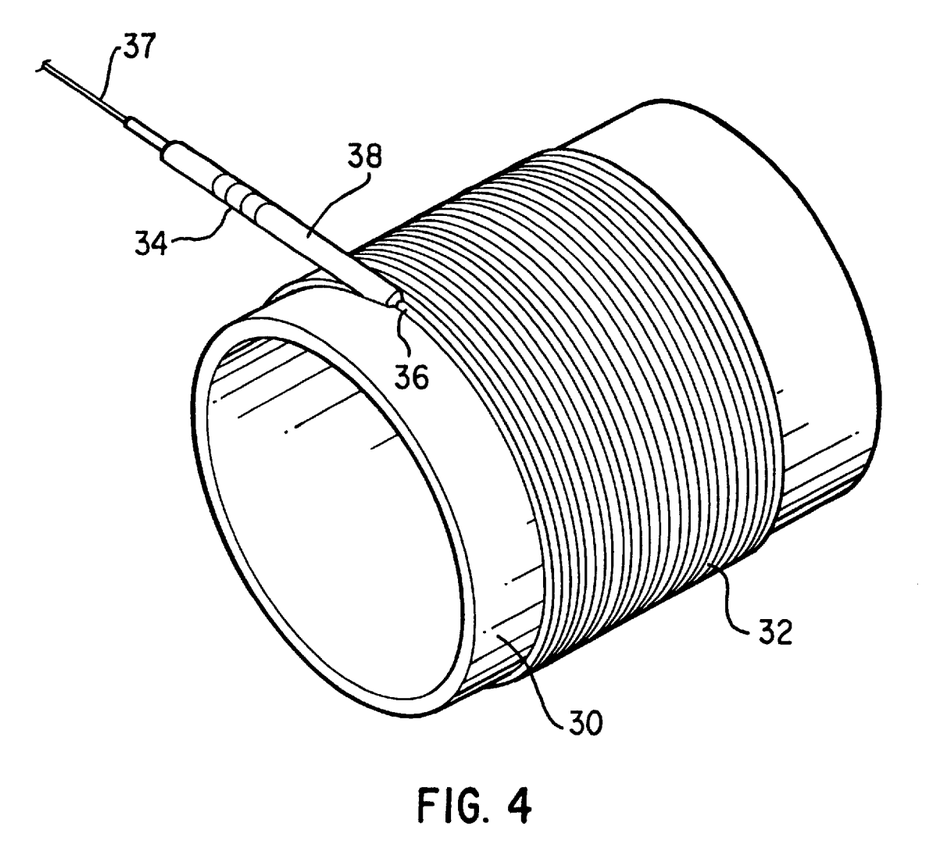
FIG. 4 is a plan view of a rigid capillary assembly for retaining a multi-capillary tube of this invention.

The multi-capillary of this invention is suited for the spiral wound chromatography arrangement of the prior art. FIG. 4 shows a typical arrangement of this type having a mandrel 30 with multiple windings of multiple capillary tubing 32. A connector arrangement communicates an end 36 of capillary tubing 32 with metallic tubing 37 through a connector 34. A tube in the form of a silica body 38 may form an interface between the capillary tube 36 and the metallic tubing 37. The fused silica body will typically have a diameter of from 3 mm to 8 mm. Metallic tubing 37 conducts or delivers fluids or solids from the interior of the capillary tubing through connector 34 to suitable equipment for the delivery of samples or the collection and analysis of the material recovered from the capillary tubes. Additional details of the spiral wound capillary system can be found in U.S. Pat. No. 5,552,042, the contents of which are hereby incorporated by reference.

The conduit as well as fittings may be attached to the to the mandrel using an oxygen/hydrogen ($H_2/O_2$) micro torch that tacks the connector body 38 over the capillary end and onto the mandrel. A bond made of a sol gel material seals the end of the connector body in place over the mandrel and capillary end. The sol gel procedure for sealing interface tube 18 and capillary end 22 to the mandrel uses a sol gel solution consisting of a 50/50 mixture by weight of 200 proof ethyl alcohol and a silica powder containing 0.5 micrometer silica particles. The sol gel mixture undergoes shaking for 5 minutes and ultrasonic treatment for at least 30 minutes before application to the tube surfaces. The sol gel mixture is applied to the mandrel, connector body and capillary tube at ambient temperatures using a thin gauge applicator such as a wire to put droplets of the solid gel mixture over the components. Upon application the sol gel wicks into small spaces between the capillary and silica body. After the applied sol gel mixture has dried thoroughly, slow heating with a micro torch is carried out until the sol gel clarifies and the sealing bond is completed. The preferred method for bonding of the connector body, mandrel and capillary is further described in U.S. Pat. No. 5,653,777, the contents of which are hereby incorporated by reference.

Another important variant of our invention is one where a heating source is provided. The multi-capillary structure may contain a wire through one or more of the passages to provide integral heating through a stand alone multi-capillary tube. Heating may also be incorporated into the rigid mandrel assembly. This again generates heat in close proximity to the capillary winding and is quickly passed from the mandrel surface being heated directly to the windings. This makes it possible to achieve higher heating rates, which sometimes is advantageous in desorbing materials from stationary phases where there is a high heat of desorption and where the tendency of tailing during desorption is decreased by a high heating rate.

What is claimed is:

1. A multi-capillary tube comprising:
   an outer wall having a substantially circular perimeter that surrounds an axially extending open area; and
   a predetermined plurality of regular capillary passages defined by internal walls within the outer wall, wherein the regular capillary passages extend through the tube to define at least a portion of the open area, the regular capillary passages having transverse cross sections of substantially the same shape and maximum dimension across each transverse cross section that does not exceed 250 micrometers to define a regular capillary open area that accounts for at least 20% of the total transverse cross-sectional area surrounded by the outer wall, and wherein at least a portion of the regular capillaries share common internal walls.

2. The multi-capillary tube of claim 1 wherein the regular capillary passages have a substantially round cross-section and together account for not less than 90% of the total open area.

3. The multi-capillary tube of claim 2 wherein the variation in diameter taken along any two lines of direction within the substantially circular perimeter or the variation in diameter taken along any two lines of direction within the substantially circular cross section of each regular capillary passage varies by not more than 15%.

4. The multi-capillary tube of claim 1 wherein the variation between diameters of different round capillary passages varies by no more than 15%.

5. The multi-capillary tube of claim 1 wherein at least 50% of the wall volume is integrally bonded.

6. The multi-capillary tube of claim 5 wherein the minimum internal wall thickness between the regular capillaries increases toward the periphery of the multi-capillary tube.

7. The multi-capillary tube of claim 6 wherein the capillaries have an essentially round cross section and the regular capillary flow area accounts for at least 95% of the total cross-sectional area surrounded by the outer wall.

8. The multi-capillary tube of claim 1 wherein the thickness of the outer wall is at least twice the minimum thickness of the internal walls.

9. The multi-capillary tube of claim 1 wherein the outer wall and the internal walls are formed from the same material.

10. The multi-capillary tube of claim 1 wherein the outer wall and the inner wall are formed from a glass comprising an alumino-silicate.

11. The multi-capillary tube of claim 1 wherein the diameter of the capillary passages does not exceed 60 micrometers.

12. The multi-capillary tube of claim 1 wherein the diameter of the outer wall is in a range of from 0.3 to 3.0 mm.

13. The multi-capillary tube of claim 1 wherein the tube is coiled over at least a portion of its length.

14. The multi-capillary tube of claim 13 wherein the coiled portion of the tube is bonded to a cylindrical mandrel.

15. The multi-capillary tube of claim 14 wherein a heating element traverses at least a portion of the tube.

16. The multi-capillary tube of claim 1 wherein a coating comprising an organic stationary phase or an inorganic stationary phase at least partially covers the interior walls of the round capillary passageways.

17. The multi-capillary tube of claim 1 wherein the regular capillary passages have a transverse dimension of at least 2 micrometers.

18. The multi-capillary tube of claim 1 wherein a metallic sleeve surrounds and compresses the outer wall.

19. A method of forming a multi-capillary tube comprising an outer wall having a substantially circular perimeter that surrounds a plurality of uniform capillary passages that have a substantially uniform cross section shape defined by internal walls within the outer wall and wherein the uniform capillary passages extend through the tube and have diameters in a range of from 2 to 250 micrometers to define at least a portion of an axial flow area, the method comprising:
   a) inserting a plurality of conduits into a surrounding tube to form a tube and conduit assembly;
   b) sealing the common openings of the conduits about one end of the tube and conduit assembly to form a drawing stock having a closed end about which all conduits are sealed from fluid flow and an opposite open end about which all conduits are open for fluid flow;
   c) heating the drawing stock to a softening temperature;
   d) simultaneously drawing the heated drawing stock and restricting fluid flow from the open end to reduce the interiors of the conduits to capillary size while preventing collapsing closure of the conduit interiors; and,
   e) collecting a multi-capillary tube from the stretched drawing stock that has a number of capillary passages substantially equal to the number of conduits.

20. The method of claim 19 wherein drawing of the heated drawing stock reduces the diameter at the open end of the drawing stock, upstream of the open end of the drawing stock, restricts gas flow out of the interiors of the conduits and thereby provides the restriction to fluid flow at the open end.

21. The method of claim 19 wherein the tube and conduit assembly comprises a glass material.

22. The method of claim 19 wherein the tube and conduit assembly comprises an alumino-silicate glass.

23. The method of claim 19 wherein the tubes have a round cross section.

24. The method of claim 23 wherein prior to drawing the tubes in the tube and conduit assembly, the conduits have a diameter in a range of from 0.5 to 1 mm and a wall thickness of from 100 to 300 micrometers.

25. The method of claim 19 wherein the conduits are arranged in the assembly as rings about a central conduit and the number of conduits in the assembly is determined by the following formula:

$$N=3n^2+3n+1;$$

where,

N=the total number conduits, and n=the number of rings of conduits around the central conduit.

26. The method of claim 19 wherein the conduits are arranged in the assembly as rings about a central conduit and the number of conduits in the assembly is determined by the following formula:

$$D=K*d$$

where

D=the inner diameter of the tube, d=the outer diameter of the conduits, and

K=the factor for determining the minimum diameter of a circle that can retain the number of inner conduits in an arrangement with a central conduit.

27. The method of claim 19 wherein the conduits near the center of the assembly have a thinner wall thickness than conduits located at the outside of the assembly.

* * * * *